United States Patent [19]
Vallelunga et al.

[11] Patent Number: 5,921,969
[45] Date of Patent: Jul. 13, 1999

[54] APPARATUS FOR SHIELDING A BUTTERFLY NEEDLE

[76] Inventors: Anthony J. Vallelunga, 213 Schoolhouse Rd, Albany, N.Y. 12203; Thomas T. Paquin, P.O. Box 410, Church St., Shaftsbury, Vt. 05262; James L. Kloss, 1180 Berne-Altamont Rd, Altamont, N.Y. 12009

[21] Appl. No.: 08/837,774

[22] Filed: Apr. 22, 1997

Related U.S. Application Data

[60] Provisional application No. 60/015,898, Apr. 22, 1996.

[51] Int. Cl.⁶ .................................................. A61M 5/00
[52] U.S. Cl. ........................ 604/263; 604/171; 604/177; 604/198; 128/919
[58] Field of Search ........................... 128/919; 604/263, 604/110, 164, 192, 165, 198, 171, 177

[56] References Cited

U.S. PATENT DOCUMENTS

| | | | |
|---|---|---|---|
| 4,170,993 | 10/1979 | Alvarez | 604/263 |
| 5,192,275 | 3/1993 | Burns | 604/263 |
| 5,279,588 | 1/1994 | Nicoletti et al. | 604/250 |
| 5,350,368 | 9/1994 | Shields | 604/263 |
| 5,501,672 | 3/1996 | Firth et al. | 604/177 |
| 5,562,631 | 10/1996 | Bogert | 604/164 |
| 5,562,636 | 10/1996 | Utterberg | 604/263 |
| 5,772,638 | 6/1998 | Utterberg et al. | 604/263 |

*Primary Examiner*—Wynn Wood Coggins
*Assistant Examiner*—Deborah Blyveis
*Attorney, Agent, or Firm*—John A. Merecki

[57] ABSTRACT

An apparatus for shielding butterfly-type needles to protect against accidental needle stick injuries after use. The apparatus includes a locking mechanism for permanently locking the needle within a shield.

1 Claim, 11 Drawing Sheets

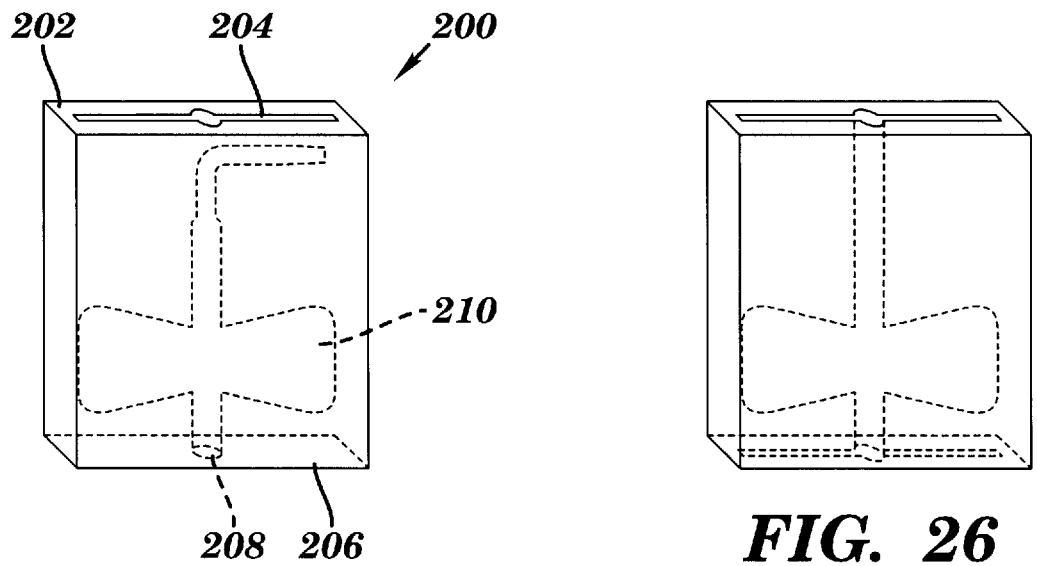
FIG. 24
FIG. 26
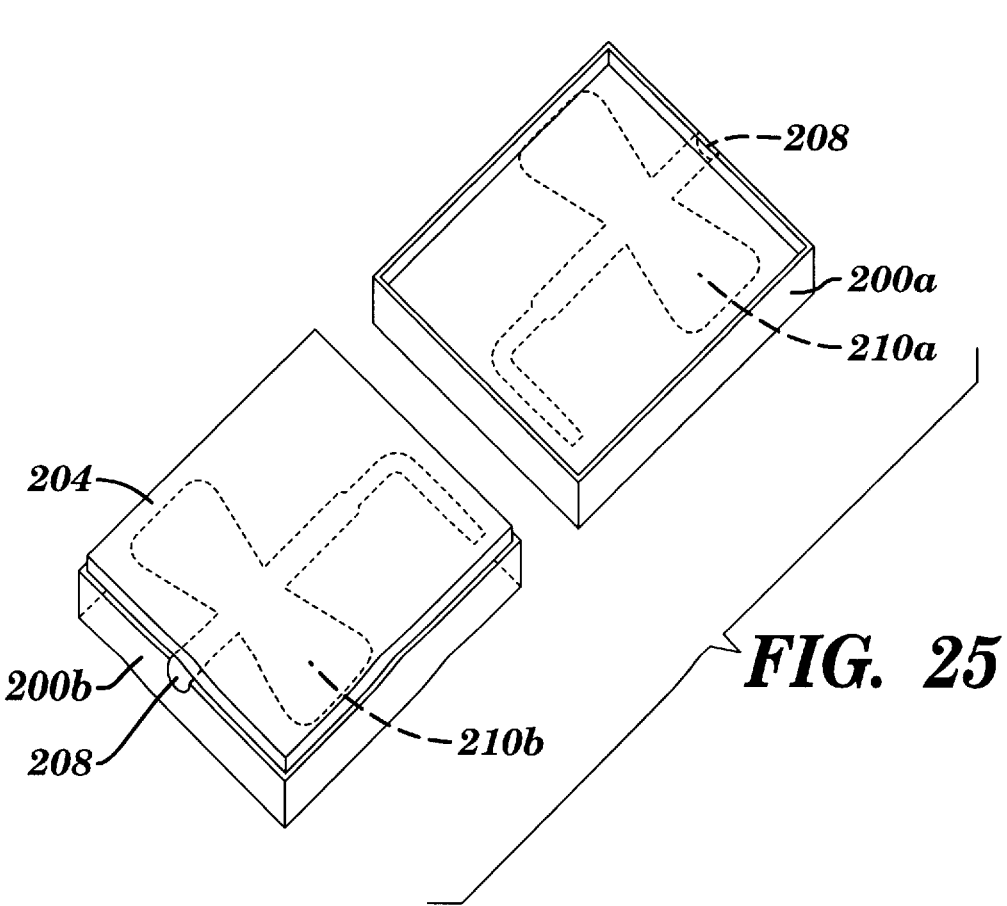
FIG. 25

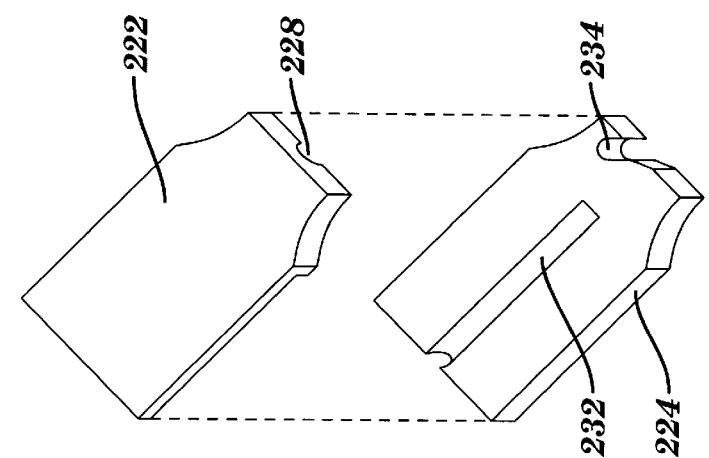
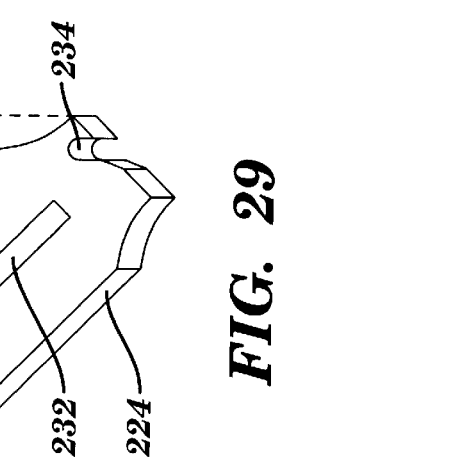
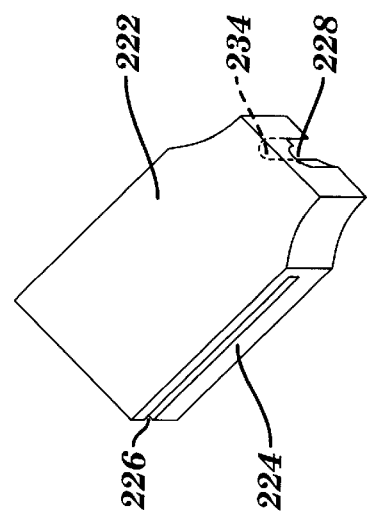
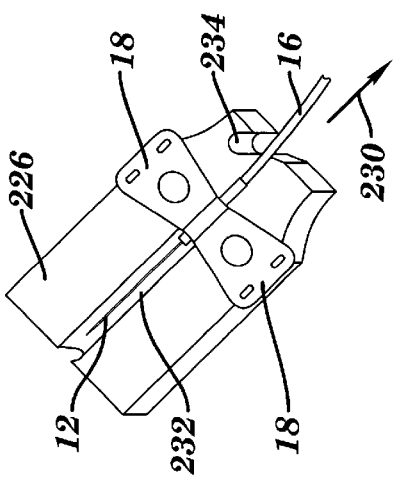
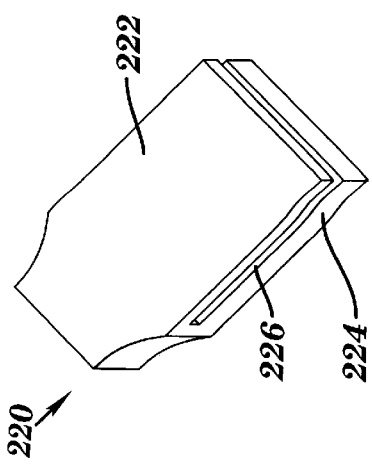

APPARATUS FOR SHIELDING A BUTTERFLY NEEDLE

This application claims benefit of provisional application 60/015,898, filed Apr. 22, 1996.

FIELD OF THE INVENTION

The present invention relates in general to the medical field. More specifically, the present invention provides an apparatus for shielding butterfly-type needles to protect against accidental needle stick injuries after use of the needle.

BACKGROUND AND SUMMARY OF THE INVENTION

Needle stick injuries pose a great risk to healthcare professionals and the public at large if the used contaminated needles are not properly handled, and disposed of, after use. Indeed, the instances of transmission of HIV (human immunodeficiency virus), hepatitis, and other potentially fatal contagious diseases has drastically increased over the last decade due to accidental needle stick injuries.

Various strategies to deal with this problem have been attempted, both for syringe needles and butterfly needles. One approach involves the use of a cap to cover the needle after use, to prevent contact with the needle. This cap can be as simple as the original plastic cap which is used to cover the needle prior to use. However, the motion required to replace the original needle cap allows for error resulting in needle contact. This is due to the relatively small diameter of the cap and the required movement of a hand toward the contaminated needle during cap replacement.

Other approaches provide for additional means, such as a shield, for covering the needle after use. Syringe needle shielding systems, for example, generally enclose the body of the syringe within a sheath designed to be longitudinally displaced over the syringe needle after use, thereby preventing multiple uses of the needle and accidental needle stick injuries. A highly effective example of a syringe shield is disclosed in U.S. Pat. No. 5,290,255 to Vallelunga et al., entitled APPARATUS FOR SHIELDING A SYRINGE NEEDLE, incorporated herein by reference. Similarly, butterfly needle shielding systems generally include some type of guard apparatus into which the butterfly needle is pulled after use. Unfortunately, currently available butterfly needle shielding systems are difficult to manufacture and use, and provide a limited degree of protection against needle stick injuries.

In order to avoid the disadvantages of the prior art, the present invention provides several embodiments of a butterfly needle shield designed to effectively prevent pricks and contact with contaminated butterfly needles.

BRIEF DESCRIPTION OF THE DRAWINGS

The features and advantages of the present invention will be evident from the following detailed description of preferred embodiments when read in conjunction with the accompanying drawings in which:

FIG. 24 illustrates an additional embodiment of a shield for use with a Huber needle;

FIG. 25 is an exploded view of the shield of FIG. 24;

FIG. 26 illustrates an embodiment of a shield for a butterfly needle which is similar in construction to the Huber needle shield of FIG. 24;

FIG. 27 is a front perspective view of a further embodiment of a shield for use with a conventional butterfly needle;

FIG. 28 is a rear perspective view of the butterfly shield illustrated in FIG. 27;

FIG. 29 is an exploded view of the butterfly shield of FIG. 27;

FIG. 30 illustrates the butterfly shield of FIG. 27 with a butterfly needle trapped therein; and FIG. 31 is a cut-away view of FIG. 29.

DETAILED DESCRIPTION OF THE INVENTION

Figure 1:
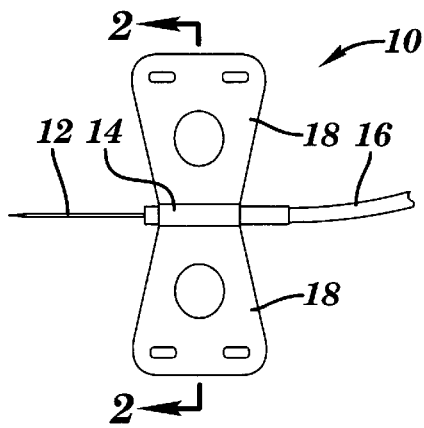
FIG. 1 illustrates a conventional butterfly needle.
Figure 2:
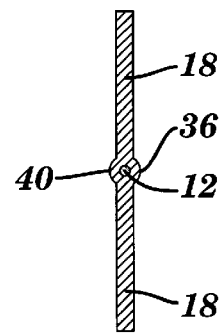
FIG. 2 is a cross-sectional view of the butterfly needle illustrated in FIG. 1, taken along line 2—2.

A typical butterfly needle 10 is shown in FIGS. 1 and 2. The butterfly needle 10 includes a hollow needle 12 mounted to a first end of a substantially tubular hub 14. A supply of flexible tubing 16 for the infusion or collection of fluid via the hollow needle 12 extends from a second end of the hub 14. The butterfly needle 10 further includes a pair of flexible, ribbed wings 18 attached to, and extending outwardly from, the hub 14. As known in the art, the wings 18 are typically folded upward and gripped together by a user during the insertion of the hollow needle 12 into a patient.

After insertion, the wings 18 are generally unfolded and taped to the skin of the patient. Clearly, upon removal from the patient, the contaminated needle 12 poses a potentially serious health risk to anyone handling the needle prior to safe disposal.

Figure 4:
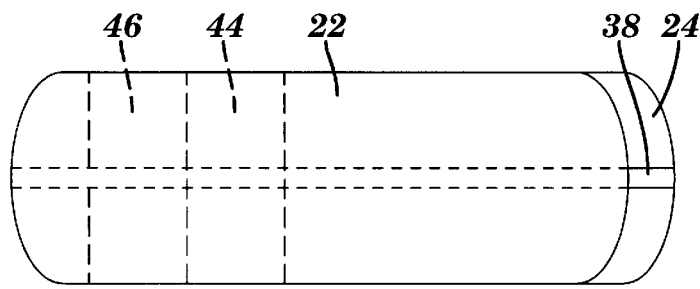
FIG. 4 is a top view of the butterfly shield illustrated in FIG. 3.
Figure 5:
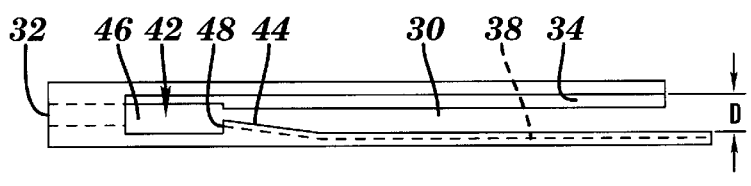
FIG. 5 is a side view of the butterfly shield of FIG. 3.
Figure 6:
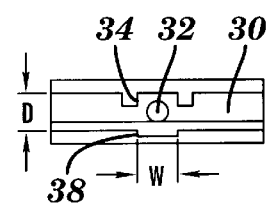
FIG. 6 is an end view of the butterfly shield of FIG. 3.

A first embodiment of a butterfly shield 20 for obviating such a health risk is illustrated in FIGS. 4–6. The butterfly shield 20 includes a top portion 22, a bottom portion 24, a front end 26, and a rear end 28. The top and bottom portions 22, 24 are spaced apart to provide a slot 30 for displaceably receiving the wings 18 of the butterfly needle 10 therethrough. The slot 30 preferably has a width slightly larger than the thickness of the wings 18 of the butterfly needle 10. This limits any transverse movement of the needle 12 as the butterfly needle 10 is drawn into and locked within the butterfly shield 20. Further, the narrow width of the slot 30 does not permit insertion of hands or fingers, which helps prevent accidental needle sticks or contact.

Figure 3:
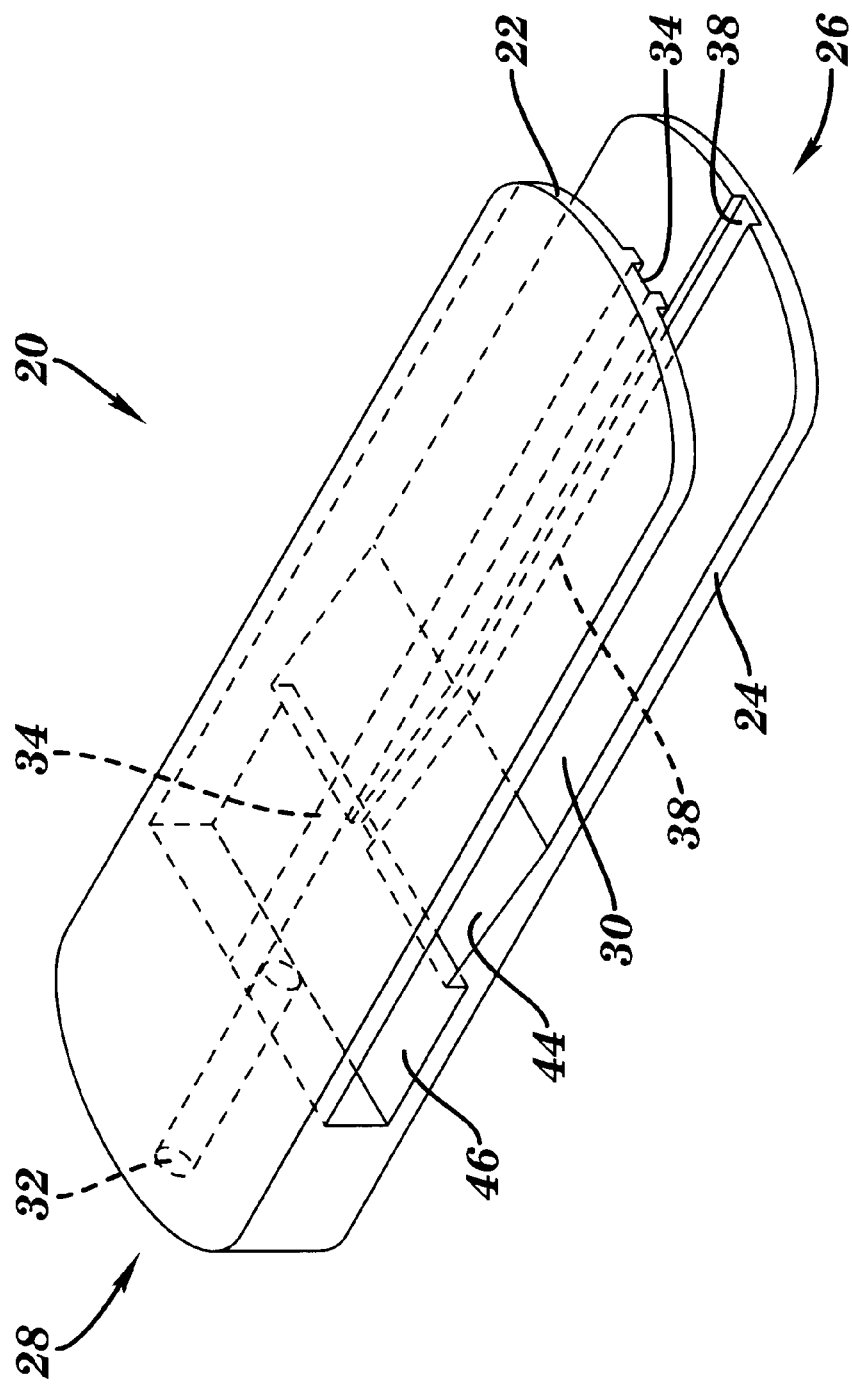
FIG. 3 is a perspective view of a butterfly shield in accordance with a first embodiment of the present invention.

As illustrated in FIG. 3, the butterfly shield 20 can be formed as a single unit from any suitable material including, but not limited to, plastic, rubber and the like. Alternately, the components of the butterfly shield 20 can be formed separately, and then joined together using a snap-fit, glue, hinge, or other appropriate method.

The butterfly shield 20 is attached to the butterfly needle 10 prior to use by slipping the end of the tubing 16 through an appropriately sized aperture 32 formed in the rear end 28 of the shield 20. The aperture 32 has a diameter slightly larger than the outside diameter of the tubing 16, thereby permitting the tubing 16 to be displaced through the aperture 32.

The top portion 22 of the butterfly shield 20 includes an interior groove 34 for guiding the upper half 36 of the hub 14 (see FIG. 2) longitudinally through the shield. Similarly, the bottom portion 24 includes an interior groove 38 for guiding the lower half 40 of the hub 14 longitudinally through the shield. Preferably, the spacing D between the grooves 34, 38, as well as the width W of the grooves 34, 38, are only slightly larger than the diameter of the hub 14 of the butterfly needle 10. This prevents the hub 14 and attached needle 12 from moving up, down, or sideways when the butterfly needle is disposed within the butterfly shield 20, thereby preventing the needle 12 from escaping the confined of shield 20.

A locking mechanism 42 is provided for securely locking the butterfly needle 10 within the butterfly shield 20 after use. The locking mechanism 42 includes a ramp 44 and a cavity 46 for capturing the butterfly needle 10. As detailed in FIGS. 3 and 4, the interior groove 34 in the top portion 22 of the butterfly shield 20 extends to the far side of the cavity 46. The interior groove 38 in the bottom portion of the butterfly shield 20, however, terminates at the apex of the ramp 44. As a consequence, the hub 14 of the butterfly needle 10, when retracted into the butterfly shield 20, passes over the ramp 44 and falls into the cavity 46 where it is locked into place by the blocking wall 48 of the ramp 44. When locked within the cavity 46 (see FIG. 9), the upper half 36 of the hub 14 remains within the longitudinally extending interior groove 34, thereby preventing any transverse displacement of the needle 12.

Figure 7:
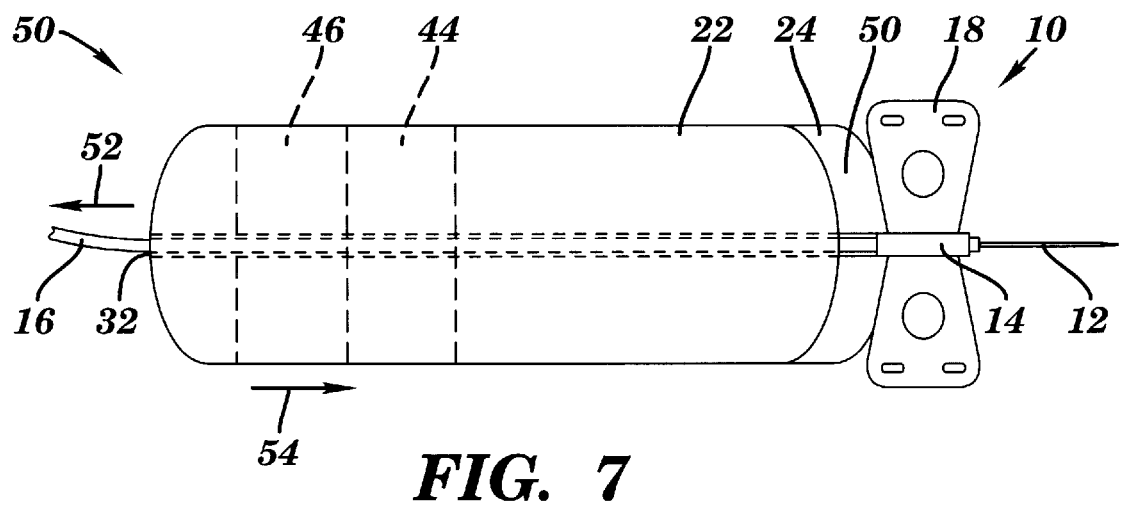
FIGS. 7–9 illustrate the operation of the butterfly needle of FIG. 3.
Figure 8:
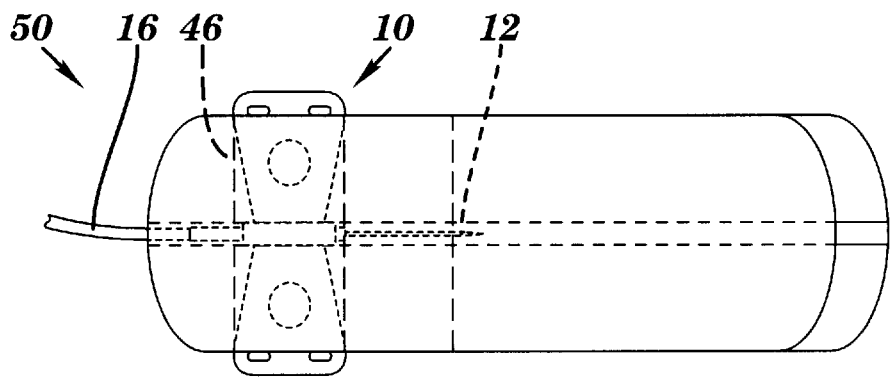
Figure 9:
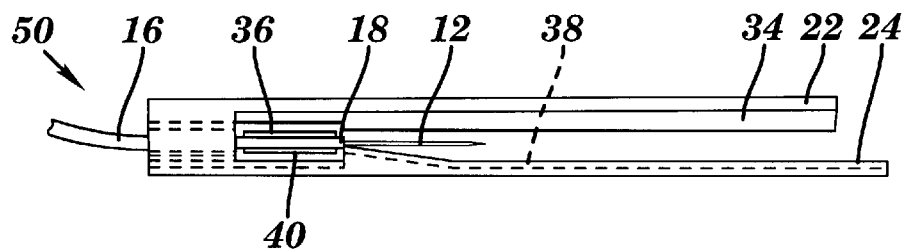

The use of the butterfly shield 20 is shown in greater detail in FIGS. 7, 8, and 9. In FIG. 7, the butterfly needle 10 is positioned on the lip 50 of the bottom portion 24 of the butterfly shield 20, with the tubing 16 inserted through the aperture 32. The lip 50 serves to initially guide the hub 14 and wings 18 of the butterfly needle 10 into the slot 30 of the butterfly shield 20. The butterfly needle 10 is retracted into the butterfly shield 20 by pulling on the flexible tubing 16 (directional arrow 52), and/or by sliding the butterfly shield 20 toward the butterfly needle 10 along the tubing (directional arrow 54), until the butterfly needle 10 is locked within the cavity 46 (FIGS. 8 and 9). As evidenced in FIGS. 8 and 9, the needle 12 of the butterfly needle 10 is safely positioned within the body of the butterfly shield 20. In accordance with the preferred embodiment of the present invention, the wings 18 of the butterfly needle extend outside of the butterfly shield 20 through opposing sides of the slot 30. However, it should be noted that the butterfly shield 20 can be formed so that the wings 18 of the butterfly needle 10 are completely enclosed within the slot 30. This can be achieved by increasing the width of the top and bottom portions 22, 24 of the butterfly shield 20.

Figure 10:
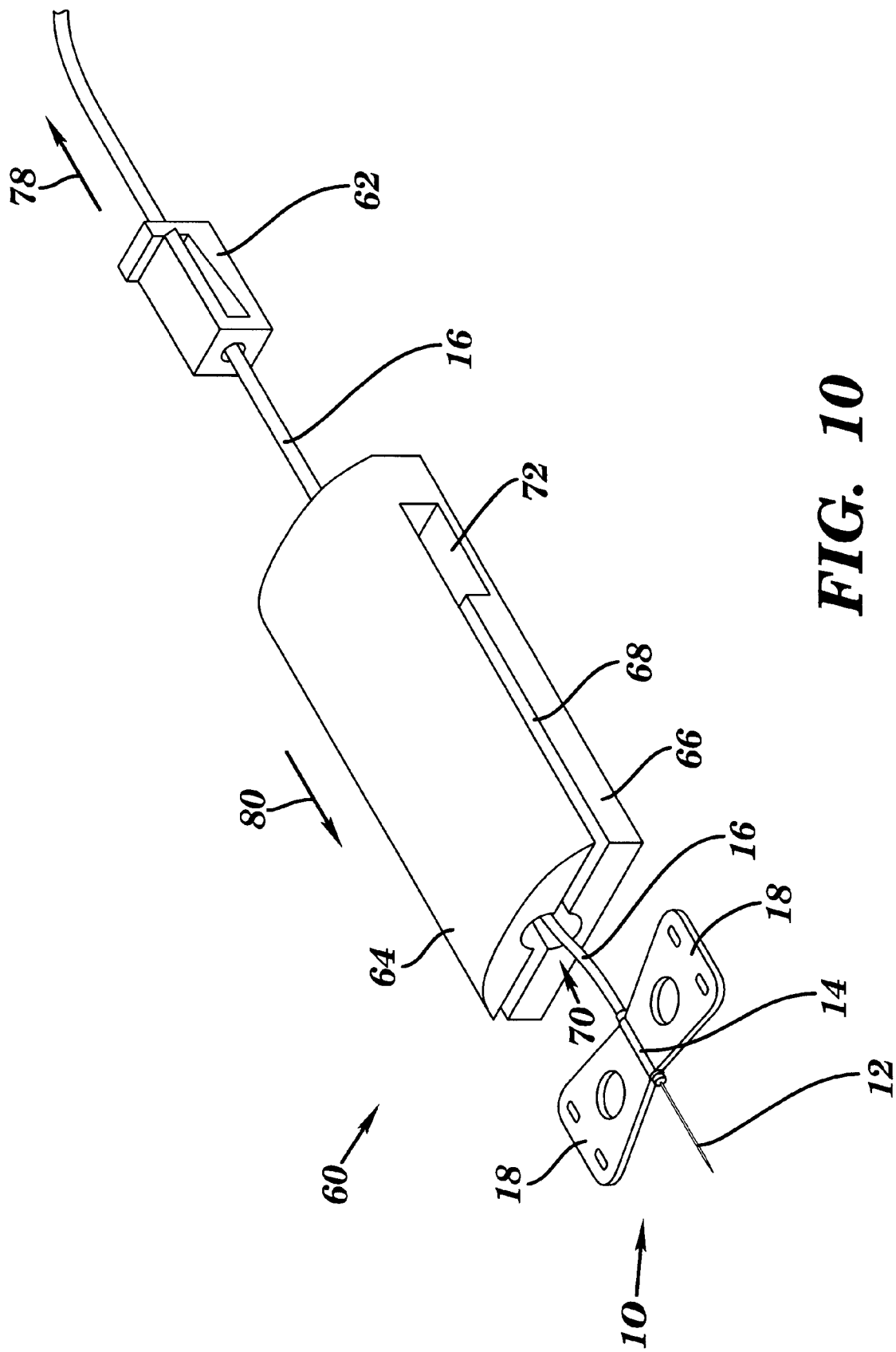
FIG. 10 is a perspective view of a butterfly shield in accordance with a second embodiment of the present invention.
Figure 11:
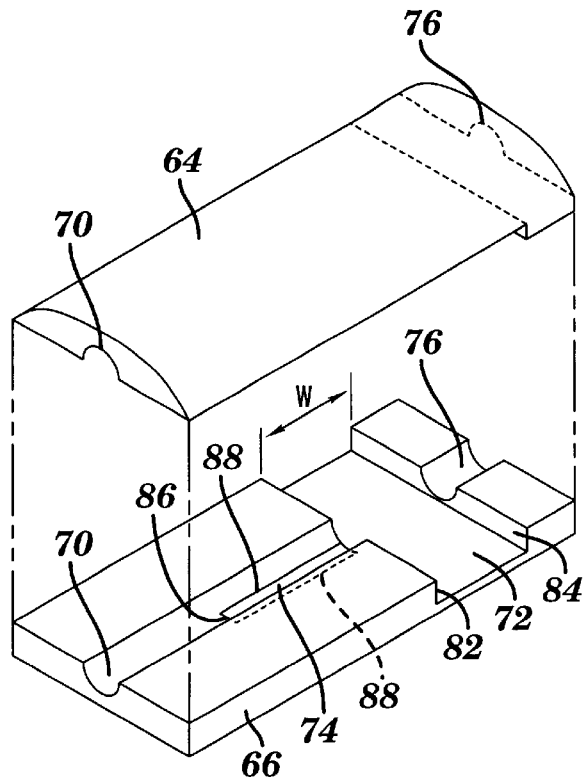
FIG. 11 is an exploded view of the butterfly shield of FIG. 10.
Figure 12:
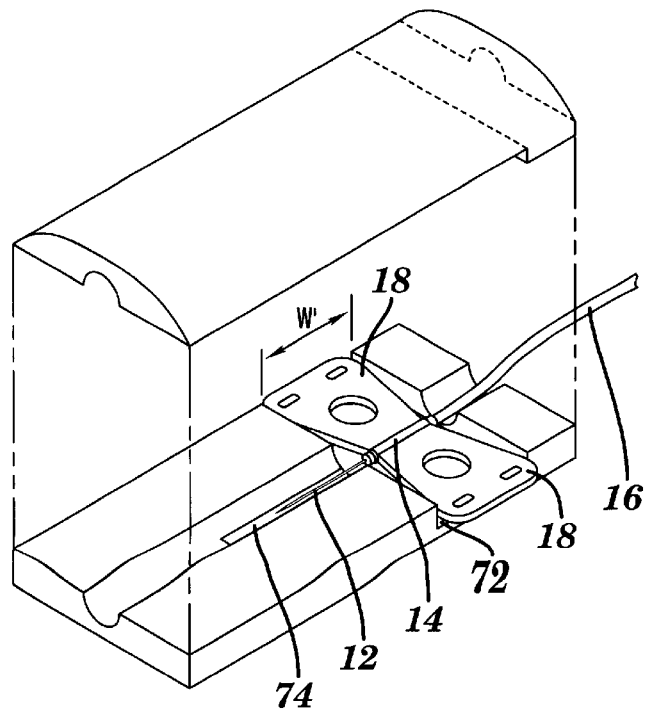
FIG. 12 is an exploded view of the butterfly shield of FIG. 10, with a butterfly needle locked therein.

A second embodiment of a butterfly shield 60 in accordance with the present invention is illustrated in FIGS. 10, 11 and 12. As with the previously described butterfly shield 20, the butterfly shield 60 is designed to capture a used butterfly needle 10 to prevent accidental needle pricks. Again, the butterfly needle 10 generally includes a hollow needle 12 mounted to a tubular hub 14, a supply of flexible tubing 16 for the infusion or collection of fluid via the hollow needle 12, and a pair of wings 18 attached to, and extending outwardly from, the hub 14. Although not previously described, the butterfly needle 10 typically further includes a clamp 62 for controlling the flow of fluid through the flexible tubing 16. The clamp 62 serves a secondary purpose when used in conjunction with the butterfly shields of the present invention. Namely, the clamp 62 can be used to position, and/or limit the displacement of, a butterfly shield along the flexible tubing 16.

Butterfly shield 60 includes a top portion 64, a bottom portion 66, and a slot 68 for separating the top and bottom portions 64, 66. The butterfly shield 60 is preferably formed (e.g., molded) as a single, integral unit. Alternately, the top and bottom portions 64, 66 of the butterfly shield 60 can be formed separately and subsequently joined using any suitable technique. The slot 68 is designed to have a width slightly larger than the width of the wings 18 of the butterfly needle 10. This allows the wings 18 to be drawn into the butterfly shield 60. The slot 68 further includes a rounded area 70 which is designed to initially receive and guide the hub 14 of the butterfly needle 10 into the butterfly shield 60.

The internal structure of the butterfly shield 60 is illustrated in FIGS. 11 and 12. As shown, the butterfly shield 60 includes a wing cavity 72 for receiving the wings 18 of the butterfly needle 10, and a needle cavity 74 for receiving and the hollow needle 12 of the butterfly needle 10. The butterfly shield 60 further includes a posterior aperture 76 through which the flexible tubing 16 of the butterfly needle 10 passes during use of the shield 60.

Operationally, the butterfly needle 10 is retracted into the butterfly shield 60 by pulling on the flexible tubing 16 (directional arrow 78), and/or sliding the butterfly shield 60 toward the butterfly needle 10 along the flexible tubing 16 (directional arrow 80), until the wings 18 and the hollow needle 12 of the butterfly needle 10 drop into, and are locked within, the wing and needle cavities 72, 74. As shown most clearly in FIGS. 11 and 12, the walls of the wing and needle cavities 72, 74 prevent the butterfly needle 10 from escaping the confined of the butterfly shield 60. Specifically, the front and rear walls 82, 84 of the wing cavity 72 prevent further displacement of the wings 18 of the butterfly needle 10 along the longitudinal axis of the butterfly shield 60. This is achieved by forming the width W of the wing cavity 72 such that it is only slightly larger than the maximum width W' of the wings 18. In a similar manner, the front and side walls 86, 88 of the needle cavity 74 prevent further longitudinal and transverse movement of a hollow needle 12.

A further embodiment of a butterfly shield 100 ("butterfly in a box") is illustrated in FIGS. 13–17. Unlike the previous embodiments of butterfly shields discussed above, the butterfly shield 100 additionally provides storage for the flexible tubing 16 of the butterfly needle 10 prior to use.

Butterfly shield 100 generally comprises a box having a front wall 102, a back wall 104, opposing side walls 106, a top 108, and a bottom 112. The top 108 includes a slot 110 which is shaped to allow the wings 18 and hub 14 of a butterfly needle 10 to enter the butterfly shield 100. The bottom 112 of the butterfly shield 100 includes an opening 114 for slidably receiving the flexible tubing 16 of the butterfly needle 10 therethrough. Preferably, the opening 114 in the bottom 112 of the butterfly shield 100 has a diameter that is slightly larger than the outside diameter of flexible tubing 16. In addition, the diameter of opening 114 is smaller than the outer diameter of the tube connector 19 located at the distal end of the flexible tubing 16. This prevents the tube connector 19 from being inadvertently pulled into the butterfly shield 100.

Figure 13:
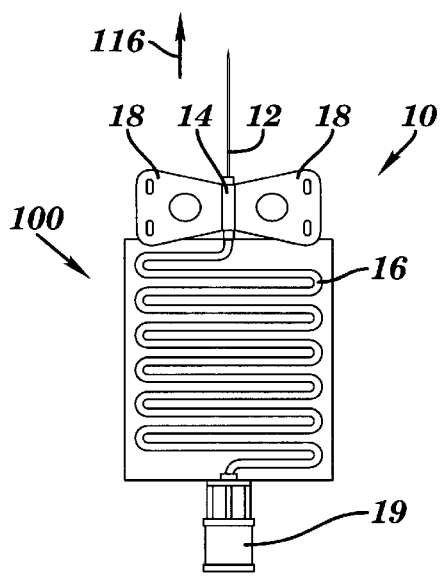
FIG. 13 illustrates a butterfly shield ("butterfly in a box") in accordance with yet another embodiment of the present invention, wherein the flexible tubing of a butterfly needle is stored within the butterfly shield prior to use.
Figure 14:
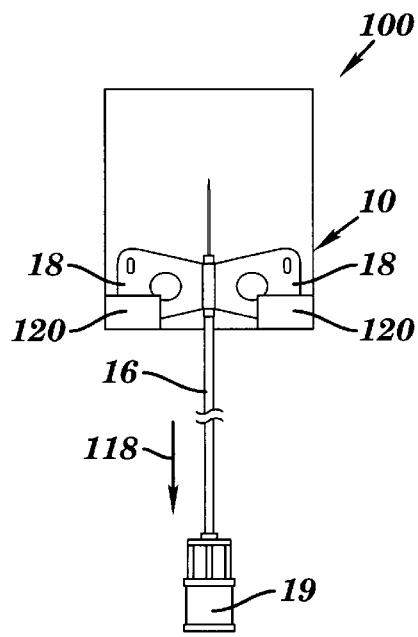
FIG. 14 illustrates the operation of the butterfly shield shown in FIG. 13.
Figure 15:
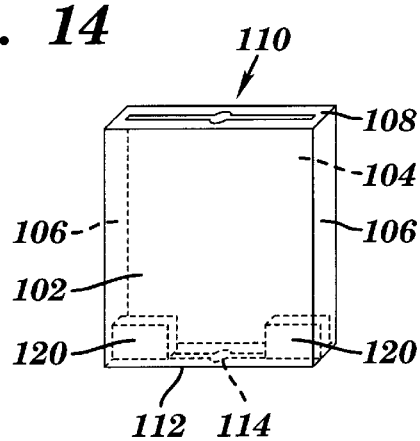
FIG. 15 is a perspective view of the butterfly shield of FIG. 13 (without the butterfly needle)

Prior to use (FIG. 13), the flexible tubing 16 of the butterfly needle 10 is preferably coiled within the butterfly shield 100, with the tube connector 19 positioned externally of the shield 100 at opening 114. Of course, it should be noted that the butterfly shield 100 can be used without initially having the flexible tubing 16 coiled inside. In this case the butterfly shield 100 is disposed on a section of the flexible tubing 16 in a manner similar to that of the butterfly shield 60 shown in FIG. 10. The remaining components of the butterfly needle 10, namely the hollow needle 12, the hub 14, and the pair of opposing wings 18, remain exposed and are located adjacent the top 108 of the butterfly shield 100. During packaging, the butterfly needle 10 can be secured to the butterfly shield 100 using tape or the like. For example, as shown in FIG. 13, the butterfly needle 10 can be secured to the shield 100 with its wings 18 partially inserted through slot 110 into the interior of the shield.

To use the butterfly needle 10, a health professional simply grasps the needle by the hub 14 or wings 18 and pulls some or all (depending on need) of the flexible tubing 16 out of the shield 100 as indicated by directional arrow 116. After extraction of the flexible tubing 16, the butterfly needle 10 can be used in a conventional manner for the infusion or collection of fluids. Advantageously, the butterfly shield 100 remains attached to the flexible tubing 16 and is readily available for the shielding of the butterfly needle 10 after use.

After the butterfly needle 10 has been removed from a patient, it can be easily and quickly locked within the butterfly shield 100 by pulling on the tubing 16 or the tube connector 19 as indicated by directional arrow 118. The butterfly needle 10 enters the body of the butterfly shield 100 after passing through the slot 110 formed in the top 108 of the shield. Within the butterfly shield 100, the wings 18 of the butterfly needle 10 lockably engage a pair of pinch clips 120 formed on interior side of the bottom 112. An example of a pinch clip 120 suitable for use in the butterfly shield 100 is illustrated in greater detail in FIG. 16. When locked into position by the pinch clips 120, the entire butterfly needle 10, including the wings 18 and the hollow needle 12, is safely enclosed within the butterfly shield 100. This prevents accidental needle pricks and/or contact with the used butterfly needle 10. The butterfly shield 100 and enclosed butterfly needle 10 can then be disposed of in a safe manner.

Figure 17:
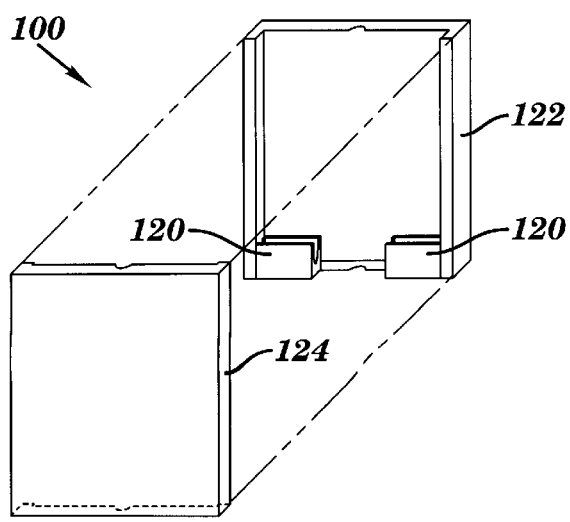
FIG. 17 is an exploded view of the butterfly shield of FIG. 15.
Figure 16:
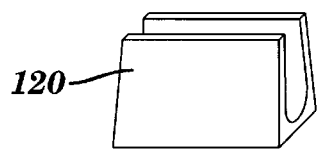
FIG. 16 illustrates a pinch-type clip used within the butterfly shield of FIG. 13 to lock a butterfly needle therein after use.

A preferred method of construction for the butterfly shield 100 is illustrated in FIG. 17. The butterfly shield 100 includes two mating sections 122, 124. This allows the flexible tubing 16 of the butterfly needle 10 to be inserted within the body of the butterfly shield 100 (e.g., as shown in FIG. 13) during manufacture of the shield.

Figure 18:
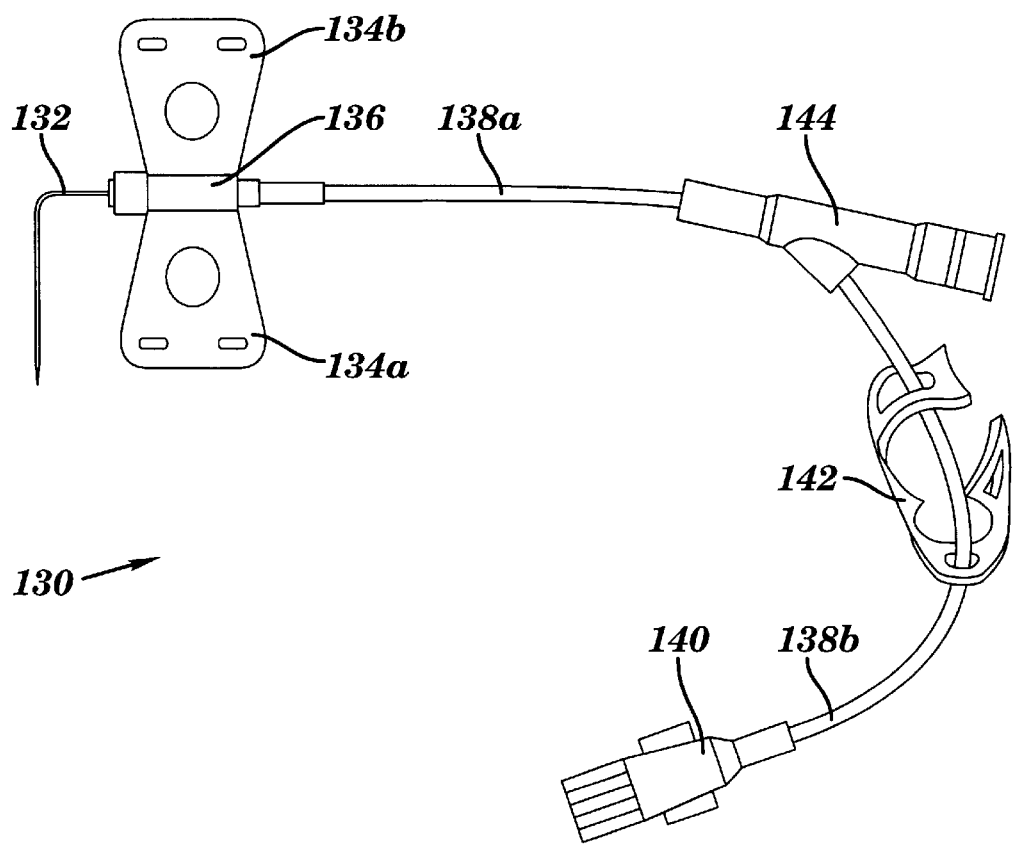
FIG. 18 illustrates a conventional Huber needle for the infusion of fluids.

A variation of the butterfly needle 10, namely a Huber needle 130, is illustrated in FIG. 18. As with the butterfly needle 10, the Huber needle 130 includes a hollow needle 132, a pair of wings 134a, 134b attached to a tubular hub 136, and a supply of flexible tubing 138a, 138b. Unlike the straight, hollow needle 12 of the butterfly needle 10, however, the hollow needle 132 of the Huber needle 130 is bent at a 90 degree angle. As a consequence, currently available butterfly shields designed for use with the butterfly needle 10 cannot be used with a Huber needle 130. The Huber needle 130 further includes a tube connector 140 for connecting the needle to an external source of fluid (e.g., an I.V. or medication), a clamp 142 for restricting fluid flow through the flexible tubing 138b, and a "Y" injection site 144.

Figure 19:
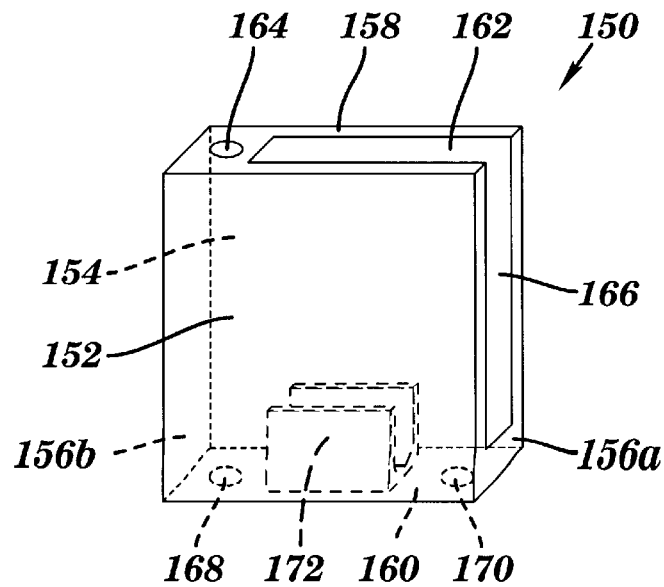
FIG. 19 is a shield in accordance with yet another embodiment of the present invention, wherein the shield is adapted for use with the Huber needle of FIG 18.

A combination container and shield 150 for the Huber needle 130 is shown in FIG. 19. The shield 150 generally comprises a box having a front wall 152, a back wall 154, opposing side walls 156a, 156b, a top 158, and a bottom 160. The top 158 includes a slot 162 which is shaped to allow wing 134a, the hub 136, and the needle 132 of the Huber needle 130 to enter the shield 150. The top 158 further includes an opening 164 for receiving flexible tubing 138b. Side wall 156a includes a slot 166 for accommodating the second wing 134b of the Cluber needle 130. The bottom 160 of the shield 150 includes a first opening 168 for receiving flexible tubing 138b, and a second opening 170 for receiving flexible tubing 138a. A pinch clip 172 extends away from the bottom 160. As described in greater detail below, the pinch clip 172 is used to lock the Huber needle 130 within the shield 150 via wing 134a. Preferably, the shield 150 is formed by permanently joining a pair of suitably formed shield sections 150a and 150b (See FIG. 20) after the Huber needle 130 has been positioned within the shield during assembly.

Figure 20:
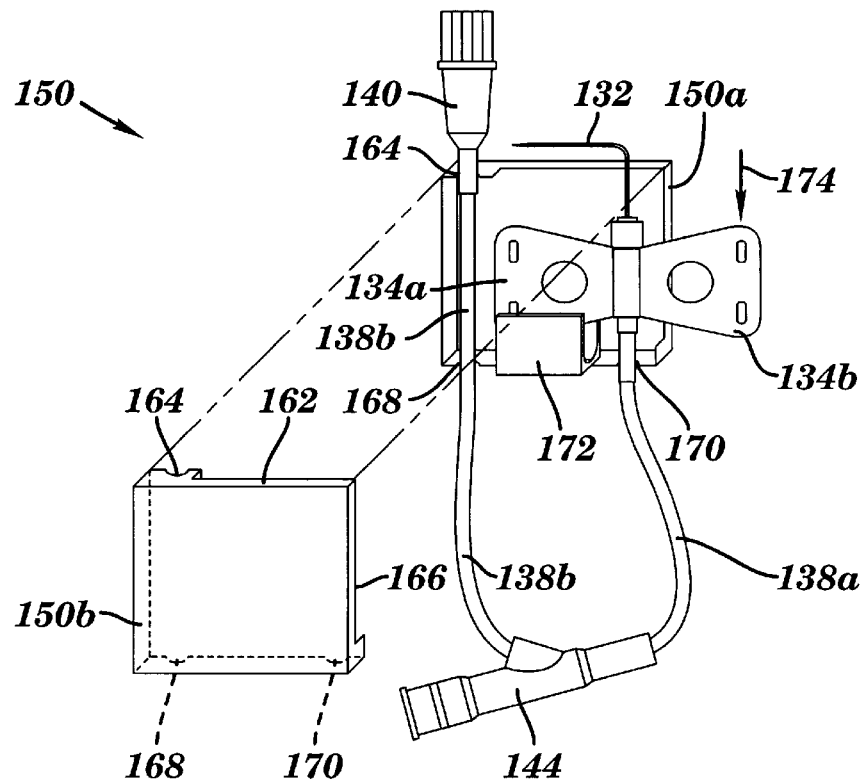
FIGS. 20 and 21 illustrate the use of the shield of FIG. 19.
Figure 21:
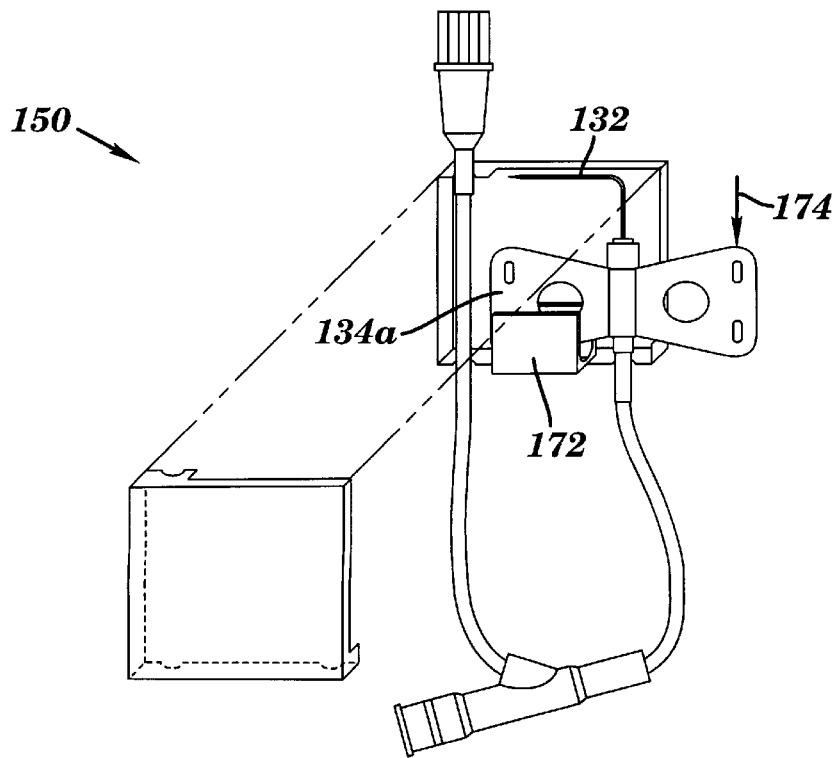

The assembly and operation of the shield 150 are illustrated in detail in FIGS. 20 and 21. During the assembly of the shield 150, the Huber needle 130 is positioned such that flexible tubing 138b passes through openings 164 and 168, with the tube connector 140 positioned adjacent (or partially inserted within) opening 164 in the top of the shield 150. Similarly, flexible tubing 138a passes through opening 170. Although not shown, it should be noted that the hollow needle 132 and wings 134a, 134b, extend fully out of the shield 150 via the slots 162, 164 prior to the use of the Huber needle 130, thereby allowing the needle to be used in a conventional manner.

After use, the Huber needle 130 is retracted into the shield 150 along direction 174. As the wings 134a, 134b enter the shield 150, wing 134a engages the pinch clip 172, while wing 134b passes through the slot 166 formed in the side wall 156a of the shield. The Huber needle 130 is retracted into the shield 150 by pulling the wing 134a and/or the flexible tubing 138a toward the shield along direction 174, until the wing 134a is fully engaged within the pinch clip 172 (FIG. 21). At this point, the hollow needle 132 of the Huber needle 130 is fully enclosed, and locked within, the shield 150. As shown in FIG. 21, the tip of the needle 132 is preferably directed away from the slot 166 in the side wall 156a of the shield 150. This offers additional protection against accidental needle stick injuries.

Figure 22:
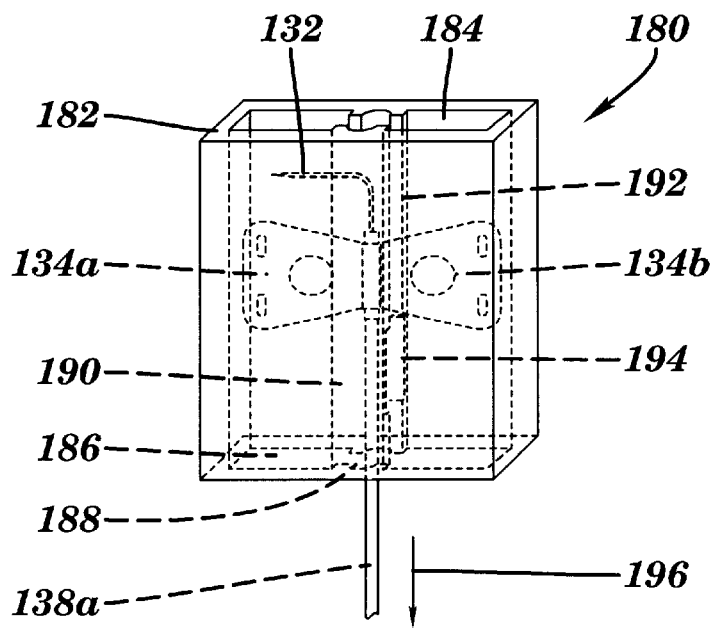
FIG. 22 shows an alternate embodiment of a shield for use with a Huber needle.
Figure 23:
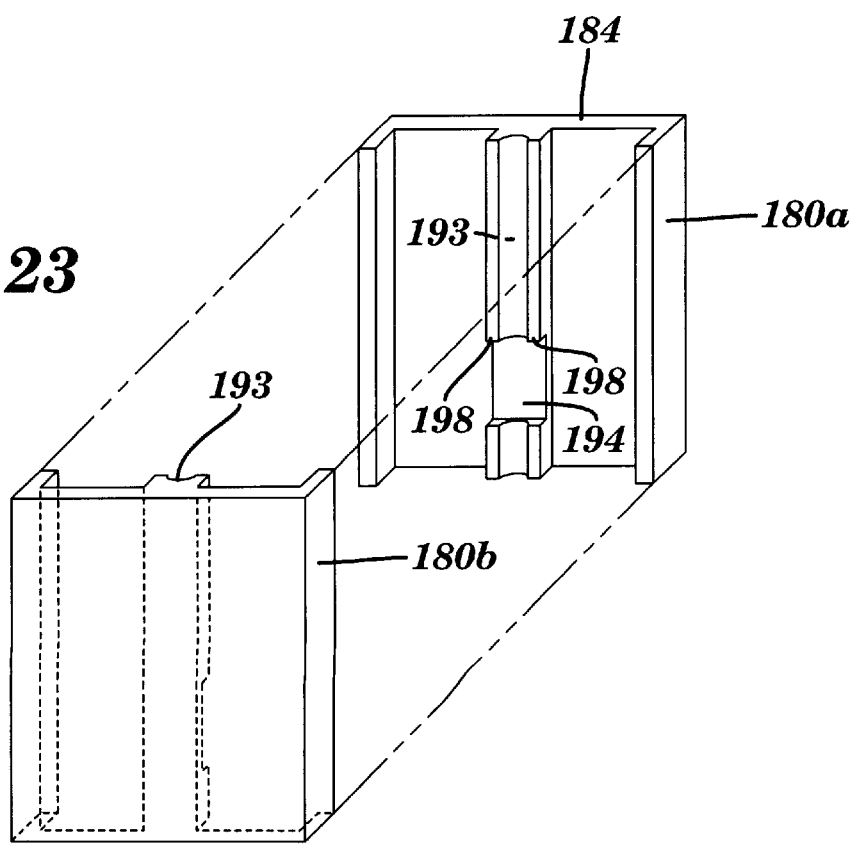
FIG. 23 is an exploded cross-sectional view of the shield illustrated in FIG. 22.

A further embodiment of a shield 180 for use with a Huber needle 130 is illustrated in FIGS. 22 and 23. When locked within the shield 180, both wings 134a, 134b and the hollow needle 132 of the Huber needle 130 are completely enclosed within the body of the shield 180.

The shield 180 generally comprises a hollow box-like structure. The top 182 of the shield 180 includes a slot 184 which is shaped to allow the wings 134a, 134b and the hub 136 of the Huber needle 130 to be drawn into the interior of the shield. The bottom 186 of the shield 180 includes an opening 188 for accommodating the flexible tubing 138a of the Huber needle 130. Enclosed between the top 182 and bottom 186 of the shield 180 is a locking mechanism 190 for guiding the Huber needle 130 into, and locking the needle within, the shield.

The locking mechanism 190 preferably includes a slot 192 and a channel 193 for guiding the wings 134a, 134b and the hub 136, respectively, of the Huber needle 130 toward a locking cavity 194. This is accomplished by pulling the flexible tubing 138a in the direction indicated by directional arrow 196. Once disposed within the locking cavity 194, the wings 134a, 134b are prevented from exiting by the blocking action of walls 198 (See FIG. 23). In this locked position, the hollow needle 132 is safely enclosed within the body of the shield 180. The shield 180 is preferably assembled by permanently joining a pair of complementary shield sections 180a and 180b (See FIG. 23) after the Huber needle 130 has been suitably positioned therebetween.

Yet another embodiment of a Huber needle shield 200 is illustrated in FIGS. 24 and 25. Once again, the shield 200 generally comprises a hollow box-like structure. The top 202 of the shield 200 includes an elongated slot 204 which allows the wings 134a, 134b, hub 136, and hollow needle 132 of the Huber needle 130 to be drawn into the interior of the shield. The bottom 206 of the shield 200 includes an opening 208 for accommodating the flexible tubing 138a of the Huber needle 130. As shown in FIG. 25, the shield 200 is preferably formed by permanently joining two complementary shield sections 200a, 200b using a snap fit, glue, or other appropriate means. A locking cavity 210, preferably formed in the shape of a Huber needle, is provided for locking the Huber needle 130 within the shield 200. In operation, the Huber needle 130 is retracted into the shield 200 by pulling on the flexible tubing 138a until the needle passes through the slot 204, and enters the locking cavity 210.

The locking cavity 210 is illustrated in greater detail in FIG. 25. The locking cavity 210 is formed by the combination of a first depression 210a in the shield section 200a, and a second depression 210b in shield section 200b, wherein each depression 210a, 210b is formed in the shape of a Huber needle. Preferably, the depression 210a in shield section 200a is deeper than the depression 210b in shield section 200b. When retracted into the shield 100, the Huber needle 130 enters the locking cavity 210 and is trapped within depression 210a. As shown in FIG. 26, the same approach can be used to shield a standard butterfly needle 10.

A final embodiment of a butterfly shield 220 for use with a standard butterfly needle 10 is illustrated in FIGS. 27–31. A front perspective view of the butterfly shield 220 is shown in FIG. 27. The butterfly shield 220 generally includes top and bottom portions 222, 224, and a slot 226 for slidably receiving the hub 14, flexible tubing 16, and wings 18 of the butterfly needle 10. The rear (FIG. 28) of the butterfly shield 220 includes an opening 228 for accommodating the flexible tubing 16. The opening 228 has a diameter slightly larger than the outside diameter of the flexible tubing. When the flexible tubing is pulled in direction 230 (FIGS. 30, 31), the butterfly needle 10 is retracted into the butterfly shield 220. To avoid needle stick injuries, the butterfly needle 10 should be retracted until the hollow needle 12 is fully enclosed within the butterfly shield 220.

A channel 232 (FIGS. 29, 31), formed in the top and/or bottom portions 222, 224 of the butterfly shield 220, guides the butterfly needle 10, via the hub 14, longitudinally into the shield. The channel 232 additionally prevents transverse displacement of the hub 14 and attached needle 12.

A locking notch 234, disposed adjacent to, and in communication with, the opening 228, is used to lock the butterfly needle 10 within the butterfly shield 220. When pulled into the locking notch 234 (FIG.31), the flexible tubing 16 is compressed and frictionally locked within the notch, thereby preventing further displacement of the butterfly needle 10. This locking action is achieved by forming the locking notch 234 such that its width is substantially smaller than the outside diameter of the flexible tubing 16.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention.

We claim:

1. An apparatus for shielding a butterfly needle having a tubular hub, a hollow needle mounted to a first end of said tubular hub, a pair of wings extending laterally away from said tubular hub, and flexible tubing extending from a second end of said tubular hub, comprising:

a front end;

a rear end having an aperture for receiving the flexible tubing of said butterfly needle therethrough;

a top portion including a longitudinally extending interior groove having a width corresponding to a width of said tubular hub, the interior groove in said top portion extending from said front end to said rear end;

a bottom portion spaced apart from said top portion a distance corresponding to the width of said tubular hub to provide a slot for receiving the wings of said butterfly needle therethrough, said bottom portion including a longitudinally extending interior groove having a width corresponding to a width of said tubular hub;

a locking mechanism for capturing said butterfly needle such that said hollow needle is protectively positioned between said top portion and said bottom portion, said locking mechanism comprising a ramp sloping upward toward said rear end and a cavity disposed between an apex of said ramp and said rear end for capturing the tubular hub of the butterfly needle, the interior groove in said bottom portion extending from said front end to said locking mechanism where it slopes upward toward the apex of said ramp;

wherein by pulling said flexible tubing through said aperture away from said rear end, the tubular hub of said butterfly needle is guided toward said locking mechanism by the interior grooves formed in said top and bottom portions, said tubular hub eventually passing over said ramp into said cavity.

* * * * *